(12) United States Patent
Utsugida

(10) Patent No.: US 11,152,102 B2
(45) Date of Patent: Oct. 19, 2021

(54) DISPLAY DEVICE AND DISPLAY METHOD

(71) Applicant: Terumo Kabushiki Kaisha, Tokyo (JP)

(72) Inventor: Tomoki Utsugida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 854 days.

(21) Appl. No.: 15/073,242

(22) Filed: Mar. 17, 2016

(65) Prior Publication Data

US 2016/0196020 A1    Jul. 7, 2016

Related U.S. Application Data

(63) Continuation of application No. PCT/JP2014/074120, filed on Sep. 11, 2014.

(30) Foreign Application Priority Data

Sep. 20, 2013  (JP) .............................. JP2013-195763

(51) Int. Cl.
  *G16H 20/40*    (2018.01)
  *G06F 3/0484*   (2013.01)
  (Continued)

(52) U.S. Cl.
  CPC .......... *G16H 20/40* (2018.01); *A61M 1/1698* (2013.01); *A61M 1/3607* (2014.02);
  (Continued)

(58) Field of Classification Search
  CPC ..... G06F 3/0484–0486; G06F 3/04847; G06F 3/0488–04886; G06F 3/048;
  (Continued)

(56) References Cited

U.S. PATENT DOCUMENTS 5,486,286 A * 1/1996 Peterson ................. A61M 1/16
                                                     210/87
9,109,945 B1* 8/2015 Warnke ............... G06F 3/04847
                        (Continued)

FOREIGN PATENT DOCUMENTS

JP          62-133645 U    8/1987
JP          09-198224      7/1997
                        (Continued)

OTHER PUBLICATIONS

Japanese Patent Office, Office Action, Application No. 2015-537892, Applicant Okazaki, Shintaro dated Nov. 15, 2017.

*Primary Examiner* — Liang Y Li
(74) *Attorney, Agent, or Firm* — MacMillan, Sobanski & Todd, LLC

(57)  ABSTRACT

A display apparatus for a user interface of a medical instrument avoids erroneous input of numerical values when a user inputs information. A display apparatus includes a numerical value information input section, a selectable target information display section, and a target selection section. A plurality of the setting information selection sections are displayed to be associated with corresponding selectable target information, and a plurality of pieces of selectable target information are arranged so as to be adjacent to each other based on a same standard. The numerical value information input section corresponding to the selected target selection section is displayed simultaneously on a same screen. A range of the selectable target information is changed visually and displayed in response to the numerical value information which is input to the numerical value information input section.

5 Claims, 9 Drawing Sheets

(51) Int. Cl.
*A61M 1/16* (2006.01)
*G16H 40/63* (2018.01)
*A61M 1/36* (2006.01)
*G06F 3/0482* (2013.01)
*G06F 40/166* (2020.01)

(52) U.S. Cl.
CPC ........ *G06F 3/0482* (2013.01); *G06F 3/04842* (2013.01); *G06F 3/04847* (2013.01); *G06F 40/166* (2020.01); *G16H 40/63* (2018.01); *A61M 2205/18* (2013.01); *A61M 2205/3331* (2013.01); *A61M 2205/3334* (2013.01); *A61M 2205/3368* (2013.01); *A61M 2205/502* (2013.01); *A61M 2205/584* (2013.01)

(58) Field of Classification Search
CPC ......... G06F 40/166–186; G06F 3/0482; G06F 3/04842; A61M 2205/18; A61M 2205/502–507; A61M 1/3607–3612; A61M 1/1698; A61M 2205/3331–3362; A61M 2205/3334; A61M 2205/3368–3372; A61M 2205/584; G16H 20/40; G16H 40/63
See application file for complete search history.

(56) References Cited

U.S. PATENT DOCUMENTS

| | | |
|---|---|---|
| 2005/0051167 A1 | 3/2005 | Biondi et al. |
| 2005/0204311 A1* | 9/2005 | Kim .................. G06F 3/0482 |
| | | 715/823 |
| 2008/0144905 A1* | 6/2008 | Tallman ............. G06F 3/04847 |
| | | 382/131 |
| 2008/0161751 A1 | 7/2008 | Plahey et al. |
| 2008/0300698 A1 | 12/2008 | Havekost et al. |
| 2010/0306694 A1 | 12/2010 | Conzola et al. |
| 2014/0146068 A1* | 5/2014 | Lala .................. G06F 3/04847 |
| | | 345/589 |

FOREIGN PATENT DOCUMENTS

| | | |
|---|---|---|
| JP | 2008173469 A | 7/2008 |
| JP | 2010-063486 | 3/2010 |
| JP | 2012-147989 | 8/2012 |
| WO | 9411093 | 5/1994 |
| WO | 0036496 | 6/2000 |
| WO | 03038566 A2 | 5/2003 |
| WO | 2007070191 A2 | 6/2007 |
| WO | 2011034790 A2 | 3/2011 |

* cited by examiner

DISPLAY DEVICE AND DISPLAY METHOD

This application is a continuation of PCT Application No. PCT/JP2014/074120, filed Sep. 11, 2014, based on and claiming priority to Japanese application no. 2013-195763, filed Sep. 20, 2013, both of which are incorporated herein by reference in their entirety.

TECHNICAL FIELD

The present invention relates to a display apparatus and a display method in which various types of information can be input, for example.

BACKGROUND ART

In the related art, a user-interface/display method in which user-friendliness and the like of inputting information is taken into consideration so as to cope with a case where various types of information are input to a medical instrument or the like by using a display unit and the like, for example, has been proposed (for example, Japanese publication JP-A-2010-63486).

SUMMARY OF INVENTION

Technical Problem

However, when a user inputs a numerical value and the like and fills in different item sections by using a display apparatus through which information can be input, an erroneous input and the like are likely to occur. Particularly, an erroneous input that occurs in a medical instrument and the like affects human lives and the like, thereby resulting in problems.

An object of the present invention is to provide a display apparatus and a display method in which an erroneous input and the like of a numerical value and the like are unlikely to occur when a user inputs information.

Solution to Problem

In order to achieve the aforementioned object, according to the present invention, there is provided a display apparatus which displays various types of information and is configured to be able to input various types of information. The display apparatus includes a numerical value information input section through which numerical value information can be input, a selectable target information display section that displays a plurality of pieces of selectable target information, and setting information selection sections that are used to select any one of the plurality of pieces of selectable target information. The plurality of setting information selection sections are displayed to be associated with the corresponding selectable target information. The plurality of pieces of selectable target information are arranged so as to be adjacent to each other based on a same standard. When any one of the plurality of setting information selection sections is selected, the numerical value information input section corresponding to the selected setting information selection section is displayed simultaneously on a same screen together with the selected selectable target information. A range of the selectable target information which is displayed on the same screen is changed visually and displayed in response to the numerical value information which is input to the numerical value information input section.

According to the above-described configuration, the plurality of setting information selection sections (for example, "a warning (high) icon" and the like for selecting a warning numerical value (high)) are displayed to be associated with the corresponding selectable target information (for example, "a warning numerical value range (high) of a bar-shape numerical value display section" and the like).

In addition, the plurality of pieces of selectable target information ("the bar-shape numerical value display section" and the like) are arranged so as to be adjacent to each other based on the same standard (for example, the degree or the like of the numerical value). For example, "the warning numerical value range (high)" and "a normal numerical value range" in "the bar-shape numerical value display section" are adjacent to each other and are arranged in accordance with the degree of the numerical value.

When any one of the plurality of setting information selection sections is selected (for example, when "the warning (high) icon" is selected), the numerical value information input section corresponding to the selected setting information selection section ("the warning (high) icon" and the like) is displayed on the same screen together with the selected selectable target information ("the warning numerical value range (high)" and the like of "the bar-shape numerical value display section").

In addition, in response to the numerical value information (for example, "32.0" or the like) which is input to the numerical value information input section, the range of the selectable target information which is displayed on the same screen is changed visually and displayed (for example, "the warning numerical value range (high)" increases, decreases, or the like).

Therefore, when a user visually recognizes "the selectable target information (for example, the warning numerical value range (high) and the like of "the bar-shape numerical value display section")" which is desired to be set, on the screen of the display apparatus and clicks "the setting information selection section (for example, "the warning (high) icon")" which is associated therewith, "the numerical value information input section" for setting "the warning numerical value range (high)" of "the bar-shape numerical value display section" is displayed simultaneously on the same screen.

When a user inputs a numerical value through "the numerical value information input section", the range of "the warning numerical value range (high)" of "the bar-shape numerical value display section" which is displayed on the same screen is changed visually and displayed.

Accordingly, a user can visually check for the result how the numerical value information which is input by the user is reflected in "the warning numerical value range (high)", and thus, it is possible to effectively prevent an erroneous input and the like caused by a user.

It is preferable that the selectable target information display section is displayed in a form of a bar shape and the pieces of selectable target information are displayed in colors different from each other.

According to the above-described configuration, the selectable target information display section is displayed in the form of the bar shape and the pieces of selectable target information are displayed in colors different from each other (for example, green (the normal numerical value range), yellow (the warning numerical value range), and red (an alarm numerical value range)). Therefore, a user can clearly grasp the selectable target information ("the warning numerical value range (high)" and the like) which the user intends to set, and thus, it is possible to more effectively prevent an erroneous input and the like caused by a user.

It is preferable to include a setting range information storage unit which stores setting range information on each piece of the selectable target information, and a permissible range determination unit which determines whether or not the numerical value information input to the numerical value information input section is within a permissible range of the setting range information. When the numerical value information is not within the permissible range of the setting range information, inputting of the numerical value information is configured to be refused.

According to the above-described configuration, when the numerical value information is not within the permissible range of the setting range information, inputting of the numerical value information is configured to be refused. Therefore, the user is prevented from erroneously inputting a numerical value which is not within the permissible range, and thus, it is possible to reliably prevent an erroneous input.

It is preferable that the setting range information is configured to be changeable based on the numerical value information which is input to the numerical value information input section.

According to the above-described configuration, setting information can be easily changed when an operator inputs the numerical value information to the numerical value information input section.

It is preferable that the selectable target information includes information on a normal range, an alarm range, and a warning range of pressure, a temperature, and a flow rate which are measured by a medical instrument.

According to the above-described configuration, the selectable target information includes the information on the normal range, the alarm range, and the warning range of the pressure, the temperature, and the flow rate which are measured by the medical instrument. Therefore, particularly, it is possible to more effectively prevent an erroneous setting of information in a medical instrument which affects human lives and the like.

It is preferable that the selectable target information has a relationship of an upper limit and a lower limit in numerical value with the corresponding selectable target information.

In order to achieve the aforementioned object, according to the present invention, there is provided a display method of a display apparatus which displays various types of information, is configured to be able to input various types of information, and includes a numerical value information input section through which numerical value information can be input, a selectable target information display section that displays the plurality of pieces of selectable target information, and setting information selection sections that are used select anyone of the plurality of pieces of selectable target information. The plurality of setting information selection sections are displayed to be associated with the corresponding selectable target information. The plurality of pieces of selectable target information are arranged so as to be adjacent to each other based on a same standard. When any one of the plurality of setting information selection sections is selected, the numerical value information input section corresponding to the selected setting information selection section is displayed simultaneously on a same screen together with the selected selectable target information. A range of the selectable target information which is displayed on the same screen is changed visually and displayed in response to the numerical value information which is input to the numerical value information input section.

It is preferable that the selectable target information has a relationship of an upper limit and a lower limit in numerical value with the corresponding selectable target information.

Advantageous Effect of Invention

As described above, according to the present invention, it is possible to provide a display apparatus and a display method in which an erroneous input and the like of a numerical value and the like are unlikely to occur when a user inputs information.

DESCRIPTION OF PREFERRED EMBODIMENTS

Hereinafter, a suitable embodiment of the invention will be described in detail with reference to the accompanying drawings and the like.

Since the below-described embodiment is a suitable specification example of the present invention, the embodiment is subjected to various types of limitations which are technically preferable. However, the scope of the present invention is not limited to the aspects thereof unless otherwise stated in the following description particularly limiting the present invention.

Figure 1:
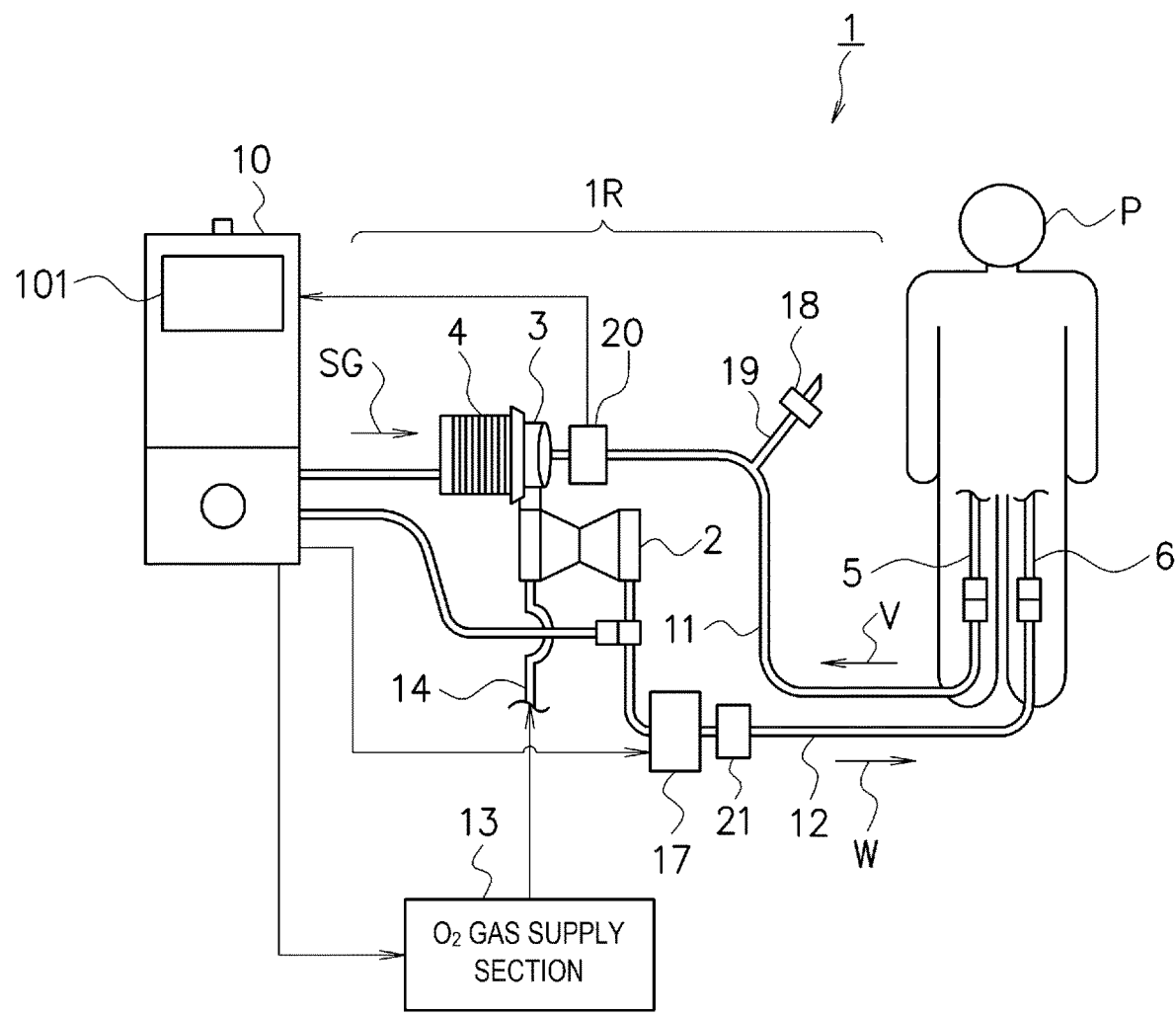
FIG. 1 is a schematic view illustrating a main configuration of an extracorporeal circulator, for example, which is a medical instrument including a controller, for example, and a display apparatus of the present invention.

FIG. 1 is a schematic view illustrating a main configuration of an extracorporeal circulator 1, for example, which is a medical instrument including a controller 10, for example, a display apparatus of the present invention.

The extracorporeal circulator 1 illustrated in FIG. 1 is an apparatus which performs extracorporeal circulation of blood of a patient P as depicted in FIG. 1. The "extracorporeal circulation" includes an "extracorporeal circulation operation" and an "assisting circulation operation".

The "extracorporeal circulation operation" denotes a circulation operation of blood and a gas exchange operation (oxygenation and/or carbon dioxide removal) with respect to blood performed by the extracorporeal circulator 1 in a case where gas exchange cannot be performed inside the body of the patient (subject) P because the heart of the patient P that is an application target of the extracorporeal circulator 1 does not circulate blood.

In addition, the "assisting circulation operation" denotes an operation additionally performed by the extracorporeal circulator 1 in order to assist the circulation operation of blood in a case where the heart of the patient (subject) P that is an application target of the extracorporeal circulator 1 circulates blood and gas exchange can be performed in the lung of the patient P. Some apparatuses have a function of the gas exchange operation performed with respect to blood.

Incidentally, the extracorporeal circulator 1 according to the present embodiment illustrated in FIG. 1 is used in a case where a cardiac surgery of the patient P is performed, for example. Specifically, a pump of the extracorporeal circulator 1 is operated so as to drain blood from the vein (the vena cava) of the patient P. After performing exchange of gas in the blood and performing oxygenation of the blood by using an artificial lung 2, "artificial lung extracorporeal blood circulation" is performed so as to return the blood to the artery (the aorta) of the patient P again. In other words, the extracorporeal circulator 1 is an apparatus which operates in place of the heart and the lung.

In addition, the extracorporeal circulator 1 has a configuration as described below. In other words, as illustrated in FIG. 1, the extracorporeal circulator 1 has "a circulation circuit 1R" which circulates blood. The circulation circuit 1R includes "the artificial lung 2", "a centrifugal pump 3", "a drive motor 4", "a vein side catheter (venous catheter) 5", "an artery side catheter (arterial catheter) 6", and the controller 10. The centrifugal pump 3 is also referred to as a blood pump.

The vein side catheter (venous catheter) 5 in FIG. 1 is inserted through the femoral vein. The distal end of the vein side catheter 5 indwells in the right atrium. The artery side catheter (arterial catheter) 6 is inserted through the femoral artery. The vein side catheter 5 is connected to the centrifugal pump 3 by using a venous tube 11. The venous tube (also referred to as "venous line") 11 is a conduit line for supplying blood.

When the drive motor 4 operates the centrifugal pump 3 in accordance with a command SG of the controller 10, the centrifugal pump 3 is configured to return blood which has been drained through the venous tube 11 and has passed through the artificial lung 2 to the patient P via a liquid supply tube 12 (also referred to as "liquid supply line").

The artificial lung 2 is arranged between the centrifugal pump 3 and the arterial tube 12. The artificial lung 2 performs the gas exchange operation (oxygenation and/or carbon dioxide removal) with respect to the blood. The artificial lung 2 is a membrane-type artificial lung, for example. It is particularly preferable to use a hollow fiber membrane-type artificial lung. Oxygen gas is supplied to the artificial lung 2 from an oxygen gas supply section 13 through a tube 14. The liquid supply tube 12 is the conduit line connecting the artificial lung 2 and the artery side catheter 6.

For example, a conduit line made from a synthetic resin such as a vinyl chloride resin and a silicone rubber, which are highly transparent and flexible can be used as the venous tube 11 and the liquid supply tube 12.

Inside the venous tube 11, blood flows in a V-direction. Inside the liquid supply tube 12, blood flows in a W-direction.

In addition, the extracorporeal circulator 1 has "a sensor unit 20" on the conduit line thereof. For example, the sensor unit 20 includes "a temperature sensor 20a", "a pressure sensor 20b", and "a flow rate sensor 20c".

Among these, the temperature sensor 20a is a sensor which measures the temperature of blood passing through the conduit line and is a sensor for detecting an abnormal temperature change and the like of blood.

The temperature of blood flowing inside the conduit line of the extracorporeal circulator 1 rises due to abnormality or the like of a cooling device. However, when the blood temperature rises, hemolysis (destruction of red corpuscles) may occur. In addition, a rise of the blood temperature leads to elevation of the body temperature of the patient P. Consequently, the oxygen consumption amount increases, and thus, there is a risk of hypoxia and the like.

Accordingly, the extracorporeal circulator 1 has the temperature sensor 20a and is configured to measure the blood temperature inside the conduit line and to issue "warning" or the like when there is a rise or the like of the temperature.

In addition, the pressure sensor 20b is a sensor which measures the pressure of blood passing through the conduit line and is a sensor for detecting an abnormal pressure of blood.

The pressure abnormality of blood often occurs due to a kink in a tube of a circulation conduit line 1R, clogging of the artificial lung 2, clogging of the centrifugal pump 3, and the like. The pressure abnormality may cause hemolysis (destruction of red corpuscles). In addition, the tube may be disconnected due to a rise of the pressure, thereby causing the possibility of a leakage or the like of blood.

The extracorporeal circulator 1 has the pressure sensor 20b and is configured to measure the blood pressure inside the conduit line and to issue "warning" or "alarm" when there is an occurrence of the pressure abnormality.

In addition, the flow rate sensor 20c is a sensor which measures the flow rate value of blood passing through the conduit line and is a sensor for detecting abnormality of the flow rate value.

Abnormality of the flow rate value occurs due to a kink in the tube of the circulation conduit line 1R, a drop in the revolution speed of the drive motor 4, an increase in pressure loss, and the like, thereby causing poor circulation of blood inside the circulation conduit line 1R. Accordingly, this may cause hypoxia and the like in a patient.

The extracorporeal circulator 1 has the flow rate sensor 20c and is configured to measure the flow rate of blood inside the conduit line and to issue "alarm" when there is an occurrence of flow rate abnormality.

As the flow rate sensor 20c, for example, an ultrasonic flow rate sensor or the like is used.

In addition, a fast clamp 17 illustrated in FIG. 1 is configured to urgently block the liquid supply tube 12 in order to stop the abnormal blood from being supplied to the patient P when flow rate abnormality or the like occurs in blood inside the conduit line.

In addition, as illustrated in FIG. 1, for example, a three-way stopcock 18 is arranged in a bifurcated tube 19 in the middle of the venous tube 11.

In this manner, the extracorporeal circulator 1 includes "the temperature sensor 20a", "the pressure sensor 20b", and "the flow rate sensor 20c" on the conduit line thereof. However, it is necessary for a user or the like, for example, a clinical engineer or the like to perform setting in advance regarding where a measurement result of the sensors is included among a normal numerical value range, a warning numerical value range (a danger range deviating slightly from the normal range), and an alarm numerical value range (a danger range deviating further from the warning range).

In a hospital and the like, the extracorporeal circulator 1 needs to be arranged for a number of different patients P and the like, and a clinical engineer or the like sets "the normal numerical value range", "the warning numerical value range", "the alarm numerical value range", and the like of the temperature, the pressure, and the flow rate which are described above, for each patient each time.

Accordingly, an erroneous input and the like may occur. The present embodiment has a configuration in which an erroneous input is unlikely to occur while performing the setting.

Regarding the setting and the like, a clinical engineer or the like performs inputting and setting by operating a touch panel-type "display unit 101 with an input device" which is the display apparatus included in the controller 10 in FIG. 1. The display unit 101 with an input device is an electronic component in which a display apparatus such as a liquid crystal panel and a position input device such as a touch pad are combined together. The display unit 101 with an input device is an input device configured to operate instruments upon displays on a screen being pressed by the clinical engineer to issue commands or to configure numerical ranges as explained above.

The controller 10 and the like of the extracorporeal circulator 1 illustrated in FIG. 1 have a computer. The computer includes a central processing unit (CPU), a random access memory (RAM), a read only memory (ROM), and the like (not illustrated), and these are connected to each other via a bus.

Figure 2:
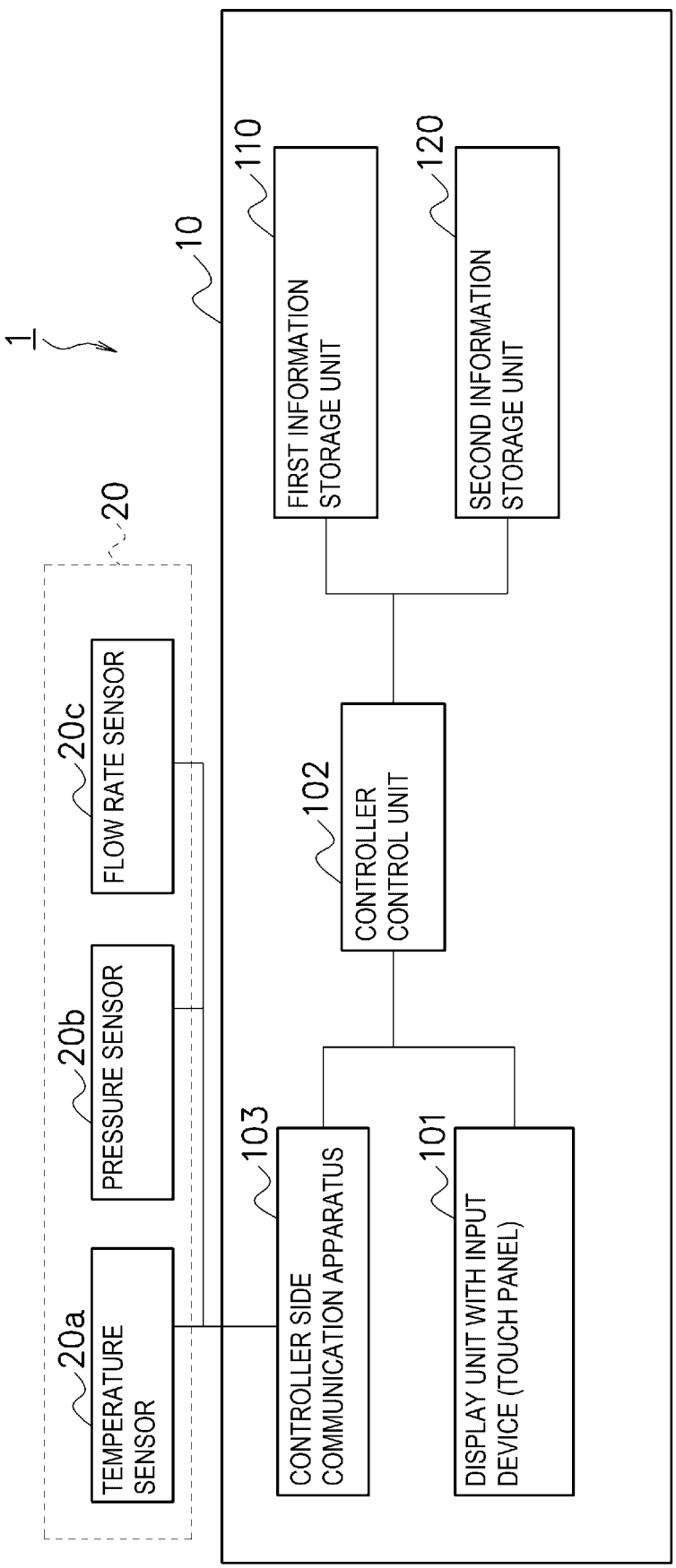
FIG. 2 is a schematic block diagram illustrating the main configuration of the extracorporeal circulator in FIG. 1.

FIG. 2 is a schematic block diagram illustrating the main configuration of the extracorporeal circulator 1 in FIG. 1. As illustrated in FIG. 2, the controller 10 has "a controller control unit 102". The controller control unit 102 controls "a controller side communication apparatus 103" for communicating with the temperature sensor 20a and the like, controls "the display unit 101 with an input device", and also controls "a first information storage unit 110" and "a second information storage unit 120".

Figure 3:
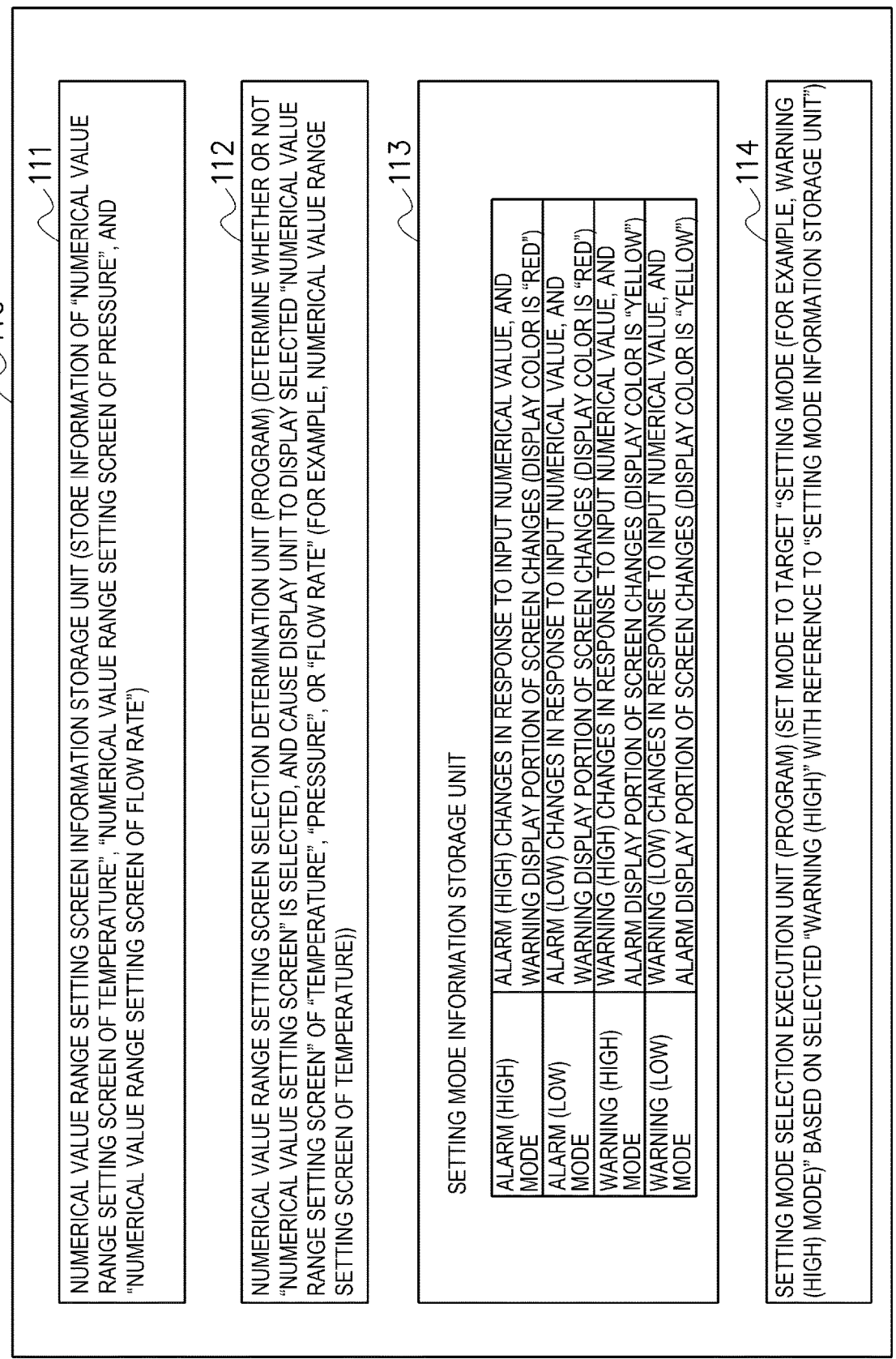
FIG. 3 is a schematic block diagram illustrating a main configuration of a first information storage unit.
Figure 4:
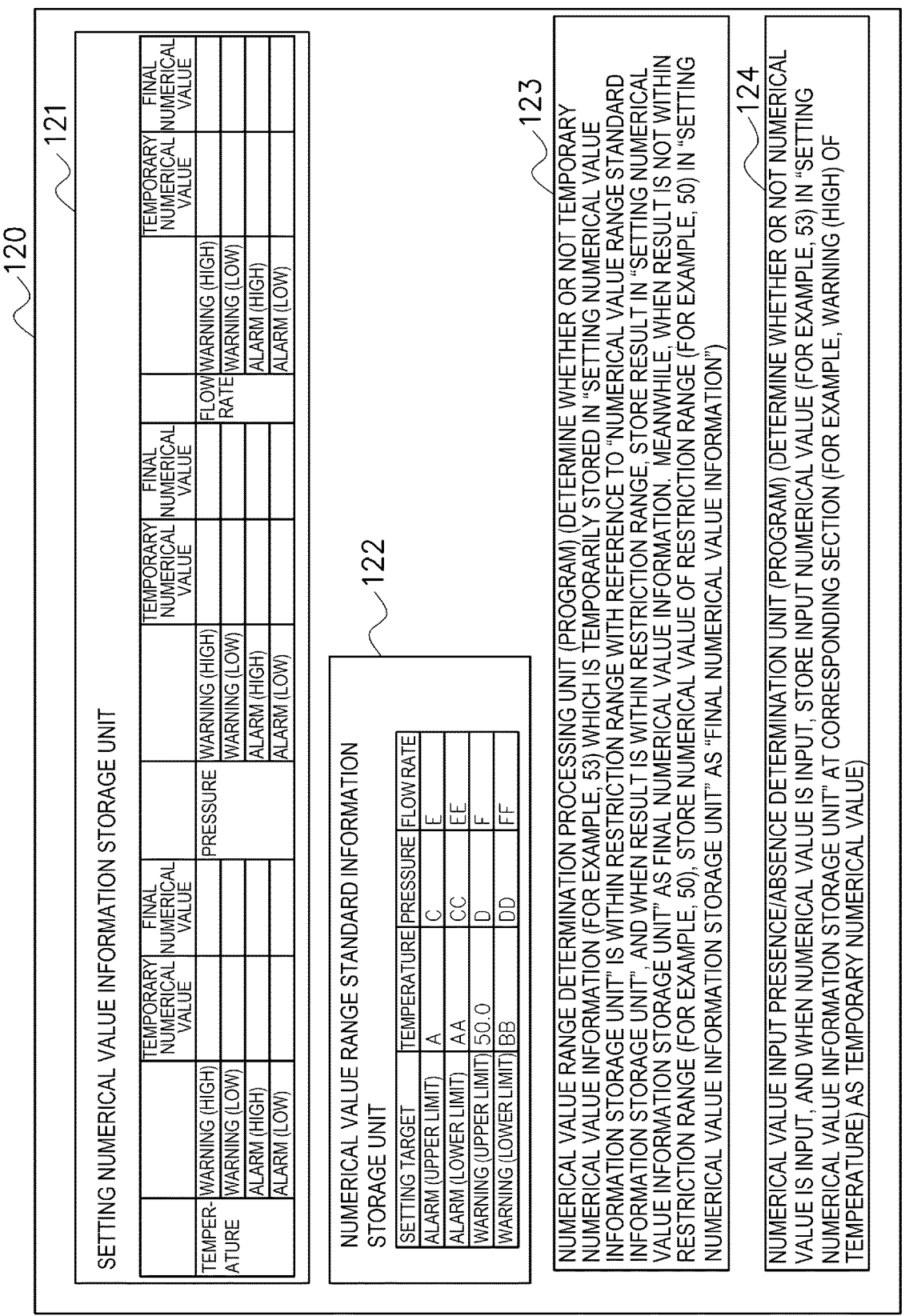
FIG. 4 is a schematic block diagram illustrating a main configuration of a second information storage unit.

FIGS. 3 and 4 are schematic block diagrams respectively illustrating main configurations of the first information storage unit 110 and the second information storage unit 120. The detailed contents thereof will be described later.

Figure 5:
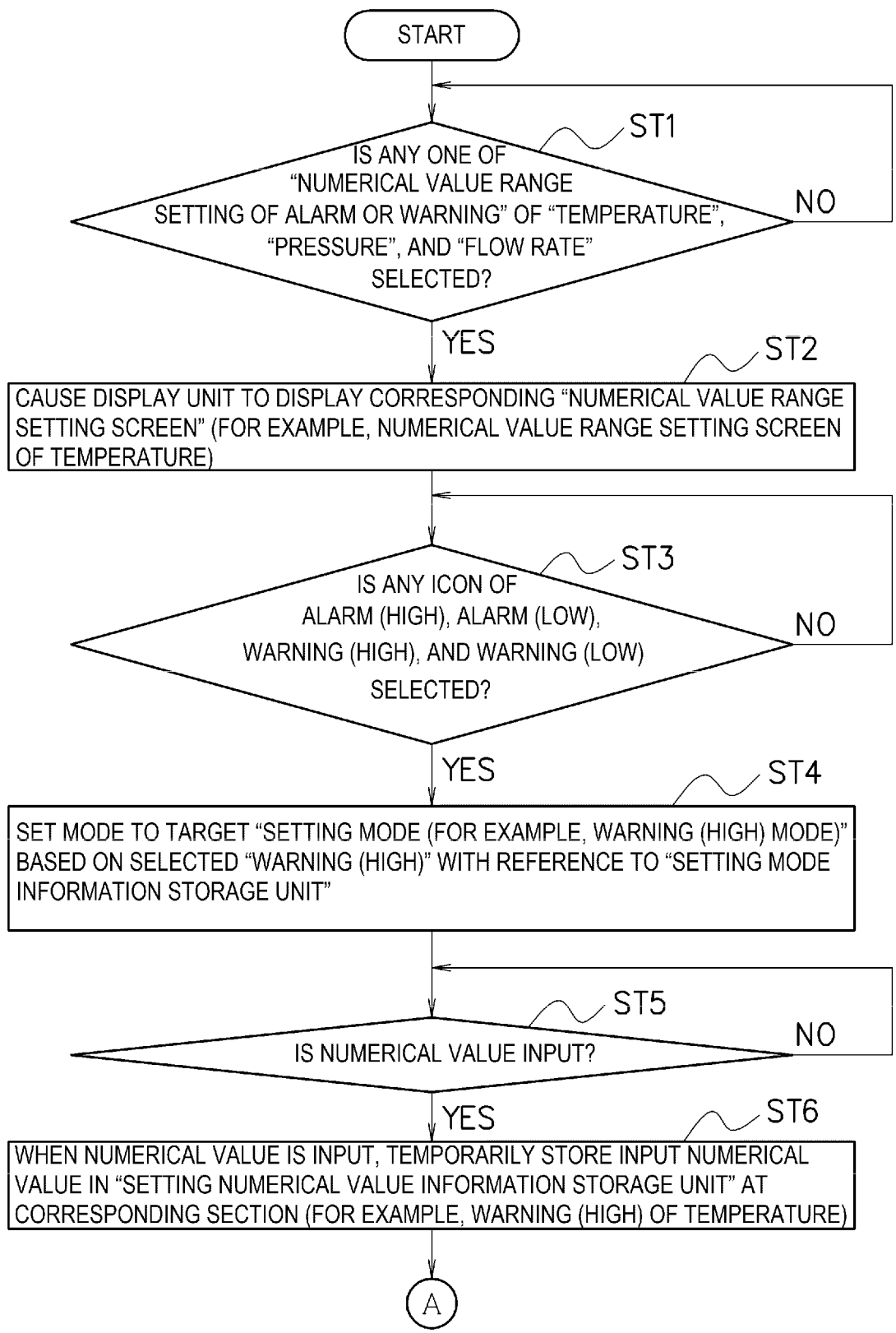
FIG. 5 is a schematic flow chart in which a main setting process and the like of a range of "warning" or the like of "temperature" and the like of blood inside a conduit line of the above-described extracorporeal circulator is shown in a display unit with an input device of FIG. 2.
Figure 6:
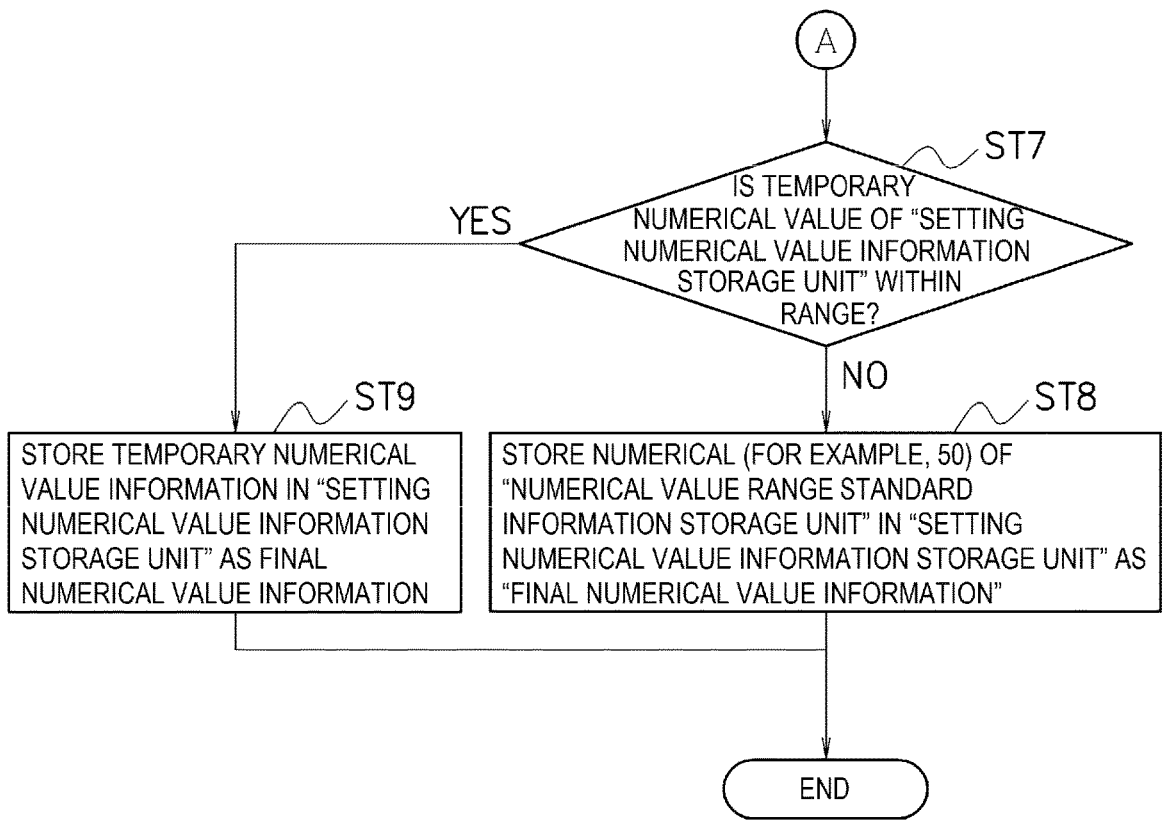
FIG. 6 is another schematic flow chart in which the main setting process and the like of the range of "warning" or the like of "temperature" and the like of blood inside the conduit line of the above-described extracorporeal circulator is shown in the display unit with an input device of FIG. 2.

FIGS. 5 and 6 are schematic flow charts in which main setting processes and the like of ranges of "warning" or the like of "temperature" and the like of blood inside the conduit line of the above-described extracorporeal circulator 1 are respectively shown in the display unit 101 with an input device of FIG. 2.

Hereinafter, description will be given along with the flow charts, and the configurations and the like in FIGS. 1, 2, and the like will be described as well.

As described above, regarding the configuration of "temperature", "pressure", and "flow rate value" of blood inside the conduit line in the extracorporeal circulator 1, a clinical engineer or the like sets "the temperature of blood", "the pressure of blood", and "the flow rate value of blood" for each patient P. When the value of the temperature sensor 20a or the like reaches the set value, a warning or the like is issued. Therefore, hereinafter, the present embodiment will be described by applying an example in which a clinical engineer or the like sets "warning" or the like of "temperature", for example.

First, the display unit 101 with an input device (hereinafter, also referred to as "display unit 101") of the controller 10 in FIG. 1 and the like displays a screen for selecting any one of "temperature", "pressure", and "flow rate value" which are subjected to setting. As used herein, "screen" refers to the contents of a graphical user interface being displayed simultaneously or together in the manner of a single page on display unit 101, wherein the screen contents may include textual or numeric information together with icons signifying active areas for user entry of other textual or numeric information. Then, the procedure proceeds to Step ST (hereinafter, referred to as "ST") 1 in FIG. 5.

In ST 1, it is determined whether or not any "numerical value range setting of alarm or warning" (numerical value setting screen) for "temperature", "pressure", or "flow rate" is selected. When it is determined that a certain "numerical value range setting of alarm or warning" (numerical value setting screen) for "temperature", "pressure", or "flow rate" is selected in ST 1, the procedure proceeds to ST 2.

In ST 2, the display unit displays the corresponding "numerical value setting screen" which has been selected (for example, a numerical value range setting screen of warning for temperature).

In other words, any selected "numerical value range setting screen" of "temperature", "pressure", or "flow rate" is displayed.

Specifically, the display unit 101 displays any selected "numerical value range setting screen" for "temperature", "pressure", or "flow rate" which is selected with reference to "a numerical value range setting screen information storage unit 111" in FIG. 3.

In other words, "the numerical value range setting screen information storage unit 111" stores information on "the numerical value range setting screens" for "temperature", "pressure", and "flow rate".

Figure 7:
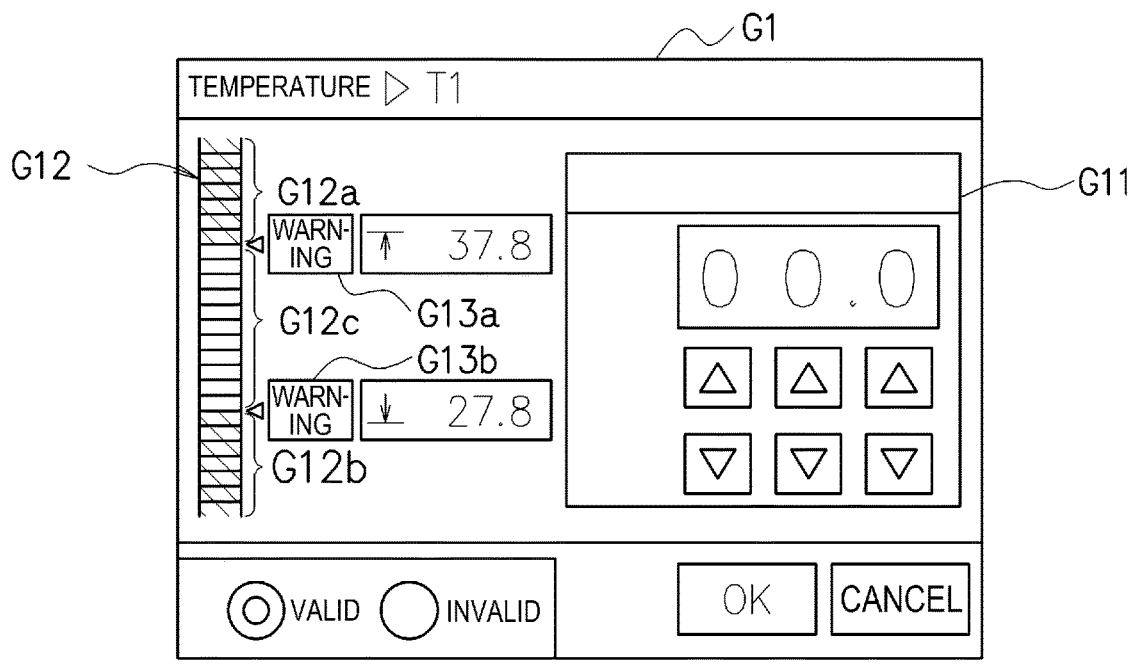
FIG. 7 is a schematic view illustrating "a temperature numerical value range setting screen" which is a numerical value range setting screen for temperature stored in "a numerical value range setting screen information storage unit".
Figure 8:
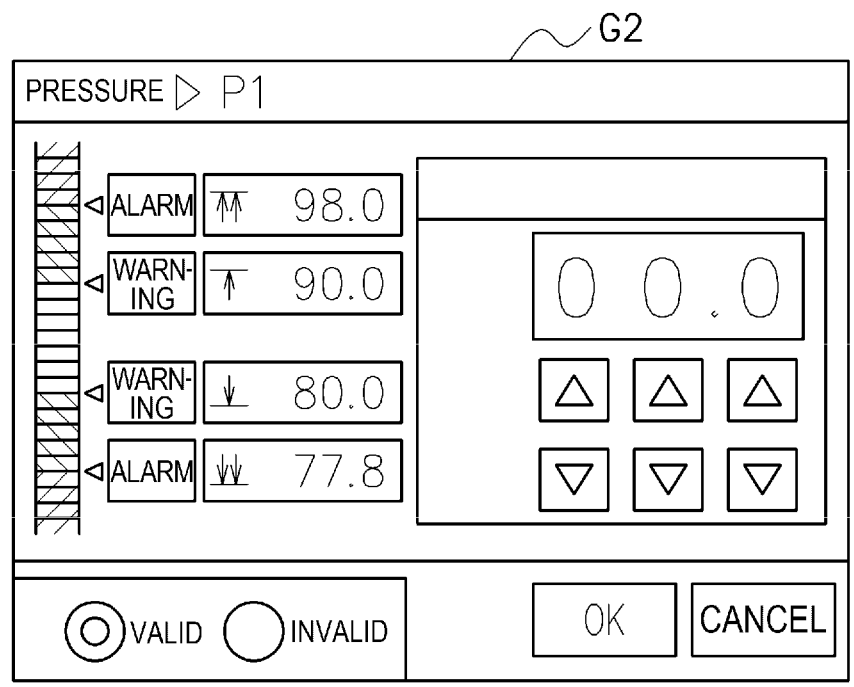
FIG. 8 is a schematic view illustrating "a pressure numerical value range setting screen" which is a numerical value range setting screen for pressure stored in "the numerical value range setting screen information storage unit".
Figure 9:
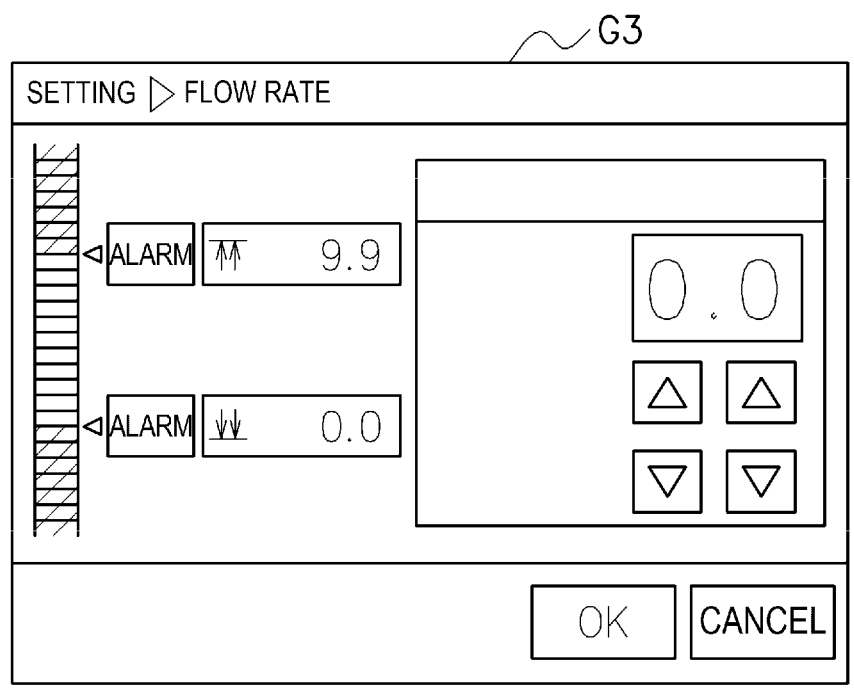
FIG. 9 is a schematic view illustrating "a flow rate numerical value range setting screen" which is a numerical value range setting screen for flow rate stored in "the numerical value range setting screen information storage unit".

FIG. 7 is a schematic view illustrating "a temperature numerical value range setting screen G1" which is a numerical value range setting screen for temperature stored in "the numerical value range setting screen information storage unit 111". FIG. 8 is a schematic view illustrating "a pressure numerical value range setting screen G2" which is a numerical value range setting screen for pressure stored in "the numerical value range setting screen information storage unit 111". In addition, FIG. 9 is a schematic view illustrating "a flow rate numerical value range setting screen G3" which is a numerical value range setting screen for flow rate stored in "the numerical value range setting screen information storage unit 111".

Among these, with reference to the temperature numerical value range setting screen G1 in FIG. 7 as an example, the display configuration thereof will be described below.

First, on the right side of the display unit 101 in FIG. 7, for example, a numerical value input section G11 which is a numerical value information input section is displayed.

In addition, on the left side of the display unit 101, for example, "a bar-shape numerical value display section G12"

which is a selectable target information display section indicating a numerical value of temperature in the form of a bar shape in the vertical direction is displayed.

The bar-shape numerical value display section G12 is divided into a warning numerical value range (high) G12a, a warning numerical value range (low) G12b, and a normal numerical value range G12c in accordance with the numerical value range thereof. The warning numerical value range (high) G12a and the warning numerical value range (low) G12b are indicated in yellow, and the normal numerical value range G12c is indicated in green.

The warning numerical value range (high) G12a, the warning numerical value range (low) G12b, and the normal numerical value range G12c are examples of selectable target information. The warning numerical value range (high) G12a, the warning numerical value range (low) G12b, and the normal numerical value range G12c are arranged so as to be adjacent to each other based on the same standard such as the numerical value. In this case, in the selectable target information, the warning numerical value range (high) G12a and the warning numerical value range (low) G12b have a relationship of the upper limit and the lower limit in numerical value.

Therefore, when numerical values are set (i.e., selected), the configuration allows a clinical engineer or the like to easily know which numerical value of the warning numerical value range (high) G12a and the warning numerical value range (low) G12b is subjected to the setting. In the selectable target information of "the pressure numerical value range setting screen G2" in FIG. 8, an alarm numerical value range (high) and an alarm numerical value range (low), and the warning numerical value range (high) and the warning numerical value range (low) respectively have relationships of the upper limit and the lower limit in numerical value.

Therefore, when numerical values are set, even though a plurality of pieces of selectable target information having the relationships of the upper limit and the lower limit in numerical value are displayed in the selectable target information display section, it is easy to know which numerical value of the numerical value range is subjected to the setting.

In addition, as illustrated in FIG. 7, on the right sides immediately next to the warning numerical value range (high) G12a and the warning numerical value range (low) G12b, for example, "a warning (high) icon G13a" and "a warning (low) icon G13b" which are setting information selection sections are arranged so as to associate with (and clearly identify) the warning numerical value ranges in the vicinity thereof.

In the present embodiment, description will be given below by applying an example in which the temperature numerical value range setting screen is selected in ST 1 and the display unit 101 displays "the temperature numerical value range setting screen G1" of FIG. 7 in ST 2.

In the processes of ST 1 and ST 2, "a numerical value range setting screen selection determination unit (program) 112" in FIG. 3 is executed.

Subsequently, the procedure proceeds to ST 3. In ST 3, it is determined whether or not a clinical engineer or the like has selected the icon of the alarm (high), the alarm (low), the warning (high), or the warning (low). According to the present embodiment, it is determined whether or not a clinical engineer or the like has selected "the warning (high) icon G13a" or "the warning (low) icon G13b" in FIG. 7.

Subsequently, the procedure proceeds to ST 4. When "the warning (high) icon G13a" is selected in ST 3, for example, "the setting mode" corresponding to the selected "warning (high)" is set with reference to "a setting mode information storage unit 113" of FIG. 3 in ST 4.

The setting mode information storage unit 113 stores information on various types of modes described below, for example.

In other words, "a warning (high) mode", "a warning (low) mode", "an alarm (high) mode", and "an alarm (low) mode" are stored.

Among these, for example, the display color of "the warning (high) mode" is yellow. In response to the numerical value which is input to the numerical value input section G11 illustrated in FIG. 7 and the like, the warning numerical value range (high) G12a of the bar-shape numerical value display section G12 in FIG. 7 fluctuates (increases/decreases). In this case, the warning numerical value range (high) G12a is also displayed in yellow. In addition, in accordance with the fluctuation of the warning numerical value range (high) G12a, the position of the warning (high) icon G13a also varies in the mode in response thereto.

The "normal numerical value range G12c" which is not within the warning numerical value range of the bar-shapes numerical value display section G12 is displayed in green, for example.

Meanwhile, in cases of "the alarm (high) mode" and "the alarm (low) mode", the display color is red.

In this manner, according to the present embodiment, since the ranges of the warning, the alarm, and the normal state are displayed in colors different from each other (yellow, red, and green), it is easy for a clinical engineer or the like to easily know and to easily observe the inputting circumstances, and thus, it is possible to effectively prevent an erroneous input.

Description will be given below by applying an example in which a clinical engineer or the like has selected "the warning (high) icon G13a" in FIG. 7 in ST 4 of the present embodiment.

Figure 10:
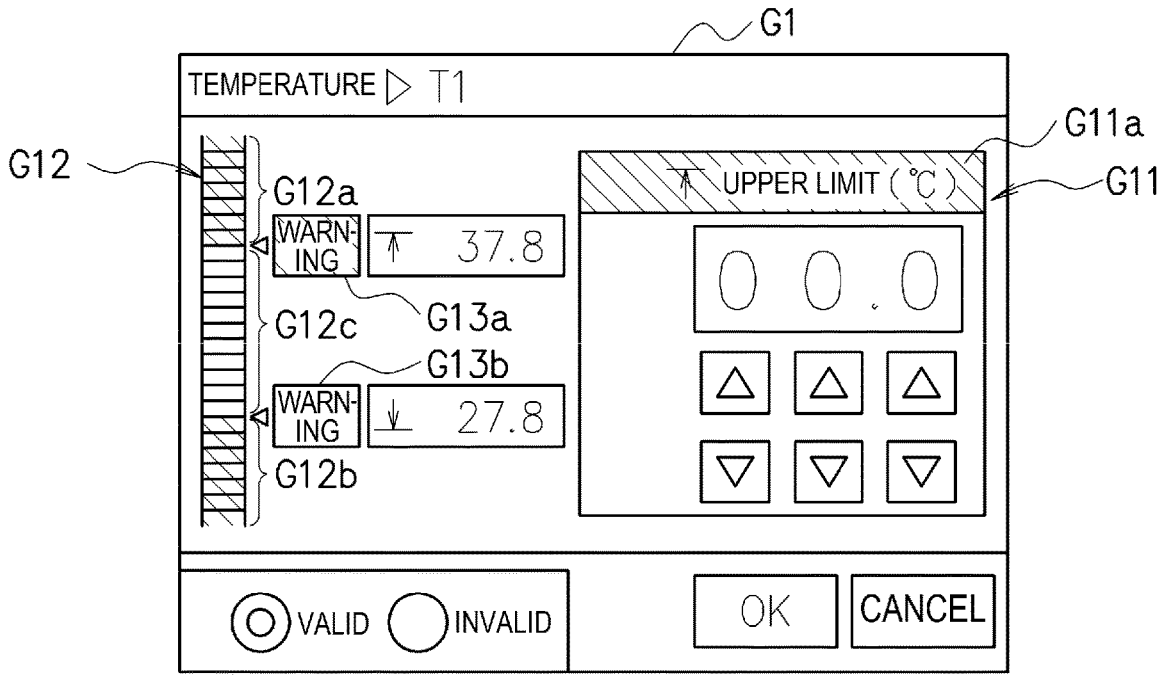
FIG. 10 is a schematic view illustrating a state where "a warning (high) mode" is in operation in the setting screen for temperature.

When a clinical engineer or the like has selected "the warning (high) icon G13a" in FIG. 7, "the warning (high) mode" of "the setting mode information storage unit 113" is in operation, and displaying of the display unit 101 is firstly changed to the screen display in FIG. 10.

FIG. 10 is a schematic view illustrating a state where "the warning (high) mode" is in operation in the setting screen for temperature.

In other words, as illustrated in FIG. 10, the display color of the warning (high) icon G13a is changed to yellow indicating the warning, and "upper limit ° C." is displayed in a portion of "a numerical value input item section G11a" of the numerical value input section G11. The "upper limit ° C." is also displayed in yellow.

Therefore, a clinical engineer or the like can clearly recognize that setting of "the warning (high)" for "temperature" is performed by the clinical engineer or the like, from the displaying of the display unit 101, and thus, an erroneous input and the like are unlikely to occur.

In addition, in this mode, not only the displaying but also the range of the warning numerical value range (high) G12a of the bar-shape numerical value display section G12 is configured to vary in response to the numerical value which is input to the numerical value input section G11.

The processes of ST 3 and ST 4 are executed by "a setting mode selection execution unit (program) 114" in FIG. 3.

Subsequently, the procedure proceeds to ST 5. In ST 5, it is determined whether or not the numerical value is input to the numerical value input section G11 in FIG. 10.

When the numerical value has been input in ST 5, the procedure proceeds to ST 6. When the numerical value is input in ST 6, the input numerical value is stored as a temporary numerical value of "the warning (high)" for "temperature" of "a setting numerical value information storage unit 121" in FIG. 4.

Subsequently, the procedure proceeds to ST 7. In ST 7, the procedure is carried out with reference to "a numerical value range standard information storage unit 122" which is a setting range information storage unit in FIG. 4, for example.

In the numerical value range standard information storage unit 122, as illustrated in FIG. 4, the upper limit and the lower limit of each of the setting ranges of the alarm (high), the alarm (low), the warning (high), and the warning (low) for pressure, temperature, and flow rate value are input in advance of connecting a patient to extracorporeal circulator 1R. In other words, the threshold values of the setting ranges are determined for the particular patient and particular procedure to be performed.

Therefore, in ST 7, the numerical value, for example, "53.0" of "the warning (high)" for "temperature" which is input and stored as the temporary numerical value is compared to the numerical value "50.0" of "the warning (high)" for "temperature" of the numerical value range standard information storage unit 122, thereby determining whether or not the temporary value "53.0" is within the range of the numerical value "50.0" of the numerical value range standard information storage unit 122.

When it is determined in ST 7 that the result is not within the range, the procedure proceeds to ST 8. In ST 8, the numerical value (for example, 50.0) of a restriction range is stored in "the setting numerical value information storage unit 121" as "final numerical value information", and the display unit 101 displays the numerical value thereof.

Figure 11:
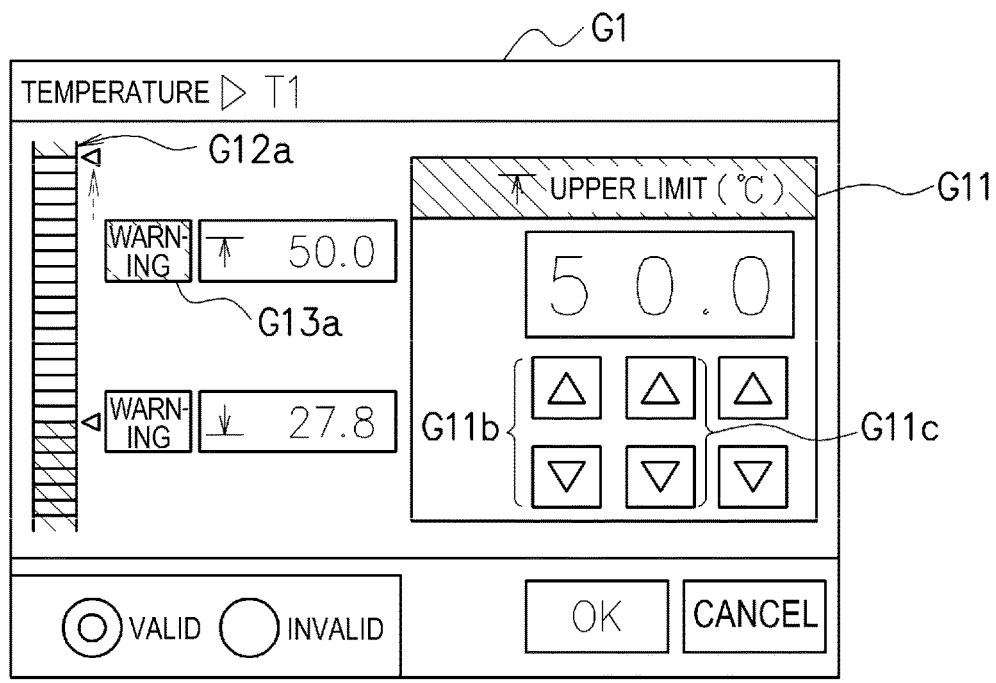
FIG. 11 is a schematic view illustrating a state where a numerical value within a restriction range is displayed.

FIG. 11 is a schematic view illustrating a state where the numerical value within the restriction range is displayed.

As illustrated in FIG. 11, in the display unit 101, the numerical value "50.0" within the restriction range is displayed in the numerical value input section G11 of the temperature numerical value range setting screen G1, and the warning numerical value range (high) G12a of the bar-shape numerical value display section G12 on the left side of the display unit 101 is also displayed in response to the numerical value.

In addition, the numerical value is displayed next to the warning (high) icon G13a in FIG. 11 in the vicinity thereof.

In this manner, according to the present embodiment, when the numerical value input by a clinical engineer or the like is not within the permissible range of numerical value range standard information, inputting of the numerical value is configured to be refused so that the proper numerical value range is retained. Therefore, it is possible to prevent a clinical engineer or the like from erroneously inputting the numerical value which is not within the permissible range, and thus, it is possible to reliably prevent such an erroneous input.

In addition, according to the present embodiment, "a ten's place increase/decrease section G1ib" which increases/decreases the digit at ten's place in the numerical value, "a one's place increase/decrease section G11c", and the like are arranged in the numerical value input section G11.

Therefore, when an operator inputs the numerical value, for example, it is possible to change the displaying in order from "45" to "46", "47", "48", "49", and "50".

According to the present embodiment, when the numerical value becomes the same as the numerical value "50.0" of "the numerical value range standard information storage unit 122", the upward arrows of "the ten's place input section G1ib" and "the one's place input section G11c" in FIG. 11 are configured to be changed into "a gray-out displaying", and thus, the operator can no longer input the numerical value.

Therefore, the operator can clearly grasp that the numerical value is the restricted upper limit or the like.

Meanwhile, in a case where the input numerical value (the temporary numerical value) is "32.0" in ST 6, for example, it is determined in ST 7 that the input numerical value is within the restriction range. The input numerical value is stored as "the final numerical value" of the setting numerical value information storage unit 121 in FIG. 4 with no change, and the display unit 101 displays the numerical value.

Figure 12:
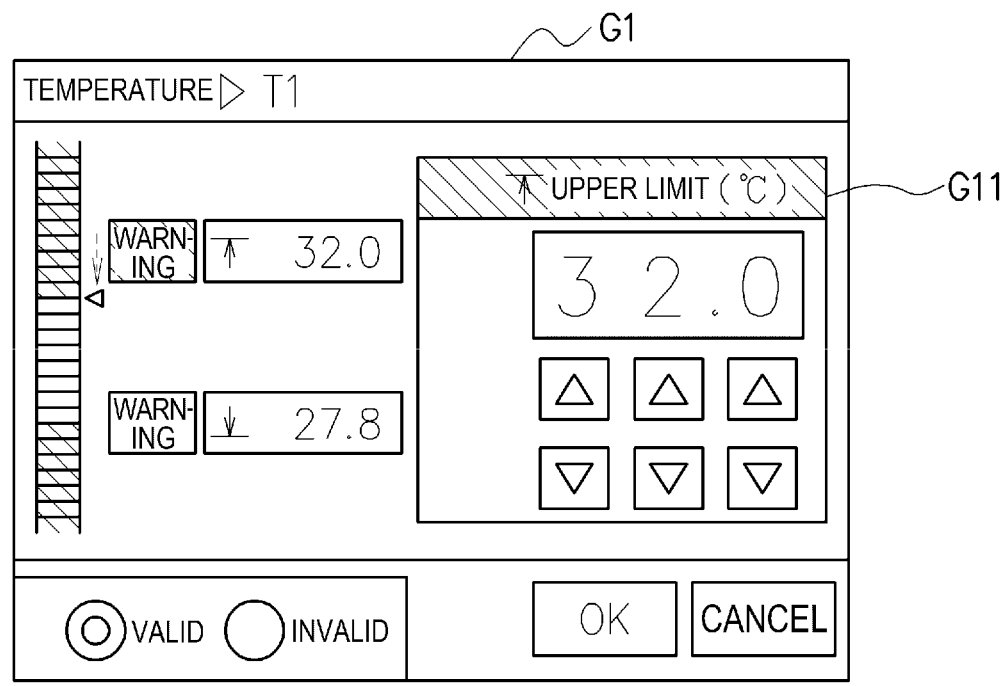
FIG. 12 is a schematic view illustrating an example in which an input numerical value (32.0) is displayed.

FIG. 12 is a schematic view illustrating an example in which an input numerical value (32.0) is displayed.

In addition, the above-described ST 5 and ST 6 are executed by a numerical value input presence/absence determination unit (program) 124 in FIG. 4. The above-described ST 7 and ST 8 are executed by "a numerical value range determination processing unit (program) 123" which is a permissible range determination unit in FIG. 4, for example.

In this manner, according to the present embodiment, when the numerical value range of "the warning (high)", "the warning (low)", "the alarm (high)", "the alarm (low)", and the like for "temperature", "pressure", and "flow rate" is set, "the numerical value input section G11" of the corresponding range is displayed by selecting "the warning (high) icon G13a" or the like. As the numerical value is input, the corresponding range of "the bar-shape numerical value display section G12" is changed visually and displayed (increasing/decreasing). In addition, the range thereof is displayed in color so as to be discriminated from others.

Therefore, the displaying is performed so as to prevent an erroneous input performed by a clinical engineer or the like. In addition, when there is an occurrence of an erroneous input which is obviously beyond the restriction range, displaying is corrected. Accordingly, it is possible to further prevent an erroneous input.

In addition, in the present embodiment described above, description is given regarding an example in which the numerical value set in advance within the restriction range is input as the numerical value of the numerical value range standard information storage unit 122 and no change is made thereafter. However, according to the present invention, the numerical value within the setting range is also configured to be changeable afterwards, as the operator operates "the ten's place input section G1ib", "the one's place input section G11c", or the like in FIG. 11.

In other words, the controller 10 has "an in-restriction range numerical value changing mode" for changing "the numerical value within the restriction range" of "the numerical value range standard information storage unit 122" in FIG. 4.

Therefore, as the operator inputs the numerical value in the mode thereof, it is possible to easily change and register "the numerical value within the restriction range".

For example, when the operator operates the upward arrow of "the one's place input section G11c" in FIG. 11, inputs the numerical value so as to change the displaying, for example, in order from "45" to "46", "47", "48", "49", and "50", and additionally inputs "51" followed by inputting of an ending signal or the like, the numerical value of "the warning (the upper limit)" of "the numerical value range standard information storage unit 122" in FIG. 4 is changed from "50.0" to "51.0", thereby being registered.

According to the present embodiment, the selectable target items are described to be "temperature", "pressure", and "flow rate". However, without being limited to the above-referenced items, blood gas, pH, concentration of potassium ion, oxygen saturation, hematocrit, hemoglobin, and the like are included as well.

Incidentally, the present invention is not limited to the above-described embodiment.

What is claimed is:

1. A display apparatus for an extracorporeal circulator monitoring various types of sensed parameters and configured to accept user input for setting warning limits and alarm limits for use during operation of the extracorporeal circulator, the display apparatus comprising:

a numerical value information input section through which numerical value information can be input;

a selectable parameter information display section that displays a plurality of ranges of a selected parameter information defined by respective upper and lower warning limits and upper and lower alarm limits, wherein each range is displayed in the form of a bar shape to show a degree of the corresponding limits, and wherein the ranges of parameter information are displayed in colors different from each other; and limit selection icons that are used to select the respective upper and lower limits of any one of the ranges of parameter information, wherein the plurality of limit selection icons are displayed in association with a corresponding range, wherein the plurality of ranges are arranged so as to be adjacent to each other, wherein when any one of the plurality of limit selection icons is selected, the numerical value information input section corresponding to the selected limit selection icon simultaneously displays a numerical value being entered by the user input on a same screen together with the selected parameter information, wherein the selected limit selection icon and at least a portion of the corresponding numerical value information input section are changed to display in a same color, and wherein the same color is yellow when the selected limit selection icon is for a warning limit and wherein the same color is red when the selected limit selection icon is for an alarm limit, and wherein the plurality of ranges of the selected parameter information which is displayed simultaneously on the same screen is changed visually by modifying a corresponding bar shape to show a modified degree of the corresponding limit in response to the numerical value being entered by the user input to the numerical value information input section before storing the numerical value being entered as a final value for monitoring the selected parameter information.

2. The display apparatus according to claim 1, further comprising:

a setting range information storage unit that stores the respective upper and lower limits for each range of parameter information; and a permissible range determination unit that determines whether or not the numerical value information which is input to the numerical value information input section is within a corresponding permissible range, wherein when the numerical value information is not within the corresponding permissible range, inputting of the numerical value information is configured to be refused.

3. The display apparatus according to claim 2, wherein the respective upper and lower limits are configured to be changeable based on the numerical value information which is input to the numerical value information input section.

4. The display apparatus according to claim 1, wherein each range of parameter information includes information on a normal range, an alarm range, and a warning range of a pressure, a temperature, and a flow rate which are measured by the medical instrument.

5. A display method of a display apparatus for an extracorporeal circulator monitoring various types of sensed parameters and configured to accept user input for setting warning limits and alarm limits for use during operation of the extracorporeal circulator, wherein the display apparatus includes a numerical value information input section through which numerical value information can be input, selectable parameter information display sections that display a plurality of ranges of selectable parameter information defined by respective upper and lower warning limits and upper and lower alarm limits, and a limit selection section that is used in order to select any one of the plurality of ranges of selectable parameter information, the method comprising the steps of:

displaying a plurality of limit selection icons in association with the corresponding ranges of selectable parameter information;

arranging the plurality of ranges of selectable parameter information so as to be adjacent to each other, wherein each range is displayed in the form of a bar shape to show a degree of the corresponding limits;

a user selecting one of the limit selection icons, wherein the selected limit selection icon and at least a portion of the corresponding numerical value information input section are changed to display in a same color, and wherein the same color is yellow when the selected limit selection icon is for a warning limit and wherein the same color is red when the selected limit selection icon is for an alarm limit;

when any one of the plurality of limit selection icons is selected, displaying the numerical value information being entered by the user input simultaneously on a same screen together with the plurality of ranges of the selected parameter information; and visually changing the displayed range of the selectable parameter information which is displayed on the same screen by modifying a corresponding bar shape to show a modified degree of the corresponding limit in response to the numerical value information which is input to the numerical value information input section before storing the numerical value information being entered as a final value for monitoring the selected parameter information.

* * * * *